United States Patent
Moinard et al.

(10) Patent No.: US 12,295,823 B2
(45) Date of Patent: *May 13, 2025

(54) METHOD FOR PROVIDING A LAMINATE WITH A HOOK AND LOOP FASTENING VOLUME, AND RESULTING LAMINATE

(71) Applicant: APLIX, Le Cellier (FR)

(72) Inventors: Nathalie Moinard, Nantes (FR); Thierry Marche, La Chapelle Basse Mer (FR)

(73) Assignee: Aplix, Le Cellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/676,445

(22) Filed: Feb. 21, 2022

(65) Prior Publication Data

US 2022/0175593 A1 Jun. 9, 2022

Related U.S. Application Data

(63) Continuation of application No. 15/301,468, filed as application No. PCT/EP2015/057441 on Apr. 7, 2015, now Pat. No. 11,357,673.

(30) Foreign Application Priority Data

| Apr. 8, 2014 | (FR) | ...................................... 1400848 |
| Jul. 16, 2014 | (FR) | ...................................... 1401591 |

(51) Int. Cl.
*A61F 13/62* (2006.01)
*A44B 18/00* (2006.01)
(Continued)

(52) U.S. Cl.
CPC ........ *A61F 13/627* (2013.01); *A44B 18/0011* (2013.01); *B32B 5/022* (2013.01);
(Continued)

(58) Field of Classification Search
CPC .... D04H 13/00; D04H 13/001; D04H 13/007; B32B 3/00; B32B 3/06; B32B 3/26;
(Continued)

(56) References Cited

U.S. PATENT DOCUMENTS

| 4,609,581 A | 9/1986 | Ott |
| 4,770,917 A | 9/1988 | Tochacek et al. |

(Continued)

FOREIGN PATENT DOCUMENTS

| DE | 2614160 A1 | 10/1977 |
| WO | WO 97/19808 A1 | 6/1997 |
| WO | WO 2008/130807 A1 | 10/2008 |

OTHER PUBLICATIONS

International Search Report dated Jun. 9, 2015 for PCT/EP2015/057441.

*Primary Examiner* — Jeremy R Pierce
(74) *Attorney, Agent, or Firm* — Renner, Kenner, Greive, Bobak, Taylor & Weber

(57) ABSTRACT

The invention relates to a laminate comprising at least one support element in the form of a non-woven fabric selected from the group consisting of an SM (Spunbond-Meltblown), an SMS (Spunbond-Meltblown-Spunbond), an SMMS (Spunbond-Meltblown-Meltblown-Spunbond), and an SSMMS (Spunbond-Spunbond-Meltblown-Meltblown-Spunbond), having a lower face and an upper face, and at least one non-woven fabric with loops made of a material comprising synthetic thermoplastic polymers, having a lower face and an upper face. The upper face of the support element is secured to the lower face of the non-woven fabric with loops. The curve representing the force required to stretch the laminate along a given axis of the laminate, as a function of elongation, includes a segment in which, starting from a zero elongation value, the force increases from zero up to a maximum force, where the maximum force corre- (Continued)

sponds to the rupture of the laminate, and the curve comprises an inflection point (Pi) on the segment.

18 Claims, 3 Drawing Sheets

(51) Int. Cl.
*B32B 5/02* (2006.01)
*B32B 5/06* (2006.01)
*B32B 5/26* (2006.01)
*D04H 13/00* (2006.01)

(52) U.S. Cl.
CPC .............. *B32B 5/06* (2013.01); *B32B 5/26* (2013.01); *D04H 13/00* (2013.01); *B32B 2262/0253* (2013.01); *B32B 2262/0261* (2013.01); *B32B 2262/0276* (2013.01); *B32B 2262/0284* (2013.01); *B32B 2262/062* (2013.01); *B32B 2262/065* (2013.01); *B32B 2555/02* (2013.01)

(58) Field of Classification Search
CPC ........... B32B 3/263; B32B 5/022; B32B 5/06; B32B 5/145; B32B 5/22; B32B 5/26; B32B 7/04; B32B 7/045; A61F 13/62; A61F 13/627; A44B 18/00; A44B 18/0003; A44B 18/0011; A44B 18/0069
See application file for complete search history.

(56) References Cited

U.S. PATENT DOCUMENTS

| | | |
|---|---|---|
| 4,854,984 A | 8/1989 | Ball et al. |
| 4,919,738 A | 4/1990 | Ball et al. |
| 5,326,612 A | 7/1994 | Goulait |
| 5,614,281 A * | 3/1997 | Jackson ............... B29C 59/022 428/152 |
| 5,643,397 A | 7/1997 | Gorman et al. |
| 5,704,101 A | 1/1998 | Majors et al. |
| 5,709,829 A | 1/1998 | Giacometti |
| 5,858,515 A | 1/1999 | Stokes et al. |
| 5,888,607 A | 3/1999 | Seth et al. |
| 6,099,932 A | 8/2000 | Gehring |
| 6,896,843 B2 | 5/2005 | Topolkaracv et al. |
| 7,303,805 B2 | 12/2007 | Seth et al. |
| 7,790,264 B2 | 9/2010 | Lester, Jr. et al. |
| 11,357,673 B2 * | 6/2022 | Moinard ................. B32B 5/06 |
| 2003/0077430 A1 | 4/2003 | Grimm et al. |
| 2006/0003658 A1 | 1/2006 | Hall et al. |
| 2006/0068167 A1 | 3/2006 | Keck et al. |
| 2007/0293112 A1 * | 12/2007 | Hanson ................. D04H 1/559 156/60 |
| 2008/0260898 A1 | 10/2008 | Lester et al. |
| 2008/0260959 A1 | 10/2008 | Gonzalez et al. |
| 2012/0231208 A1 | 9/2012 | Ducauchuis et al. |
| 2012/0247661 A1 | 10/2012 | Ogasawara et al. |
| 2015/0156705 A1 | 6/2015 | Thomas et al. |

* cited by examiner

| machine supercharging | instructions | 1 | 1.1 | 1.2 | 1.3 | 1.4 | 1.5 |
|---|---|---|---|---|---|---|---|
| inflection point | ‰ | 0 | 4 | 7 | 14 | 20 | 24 |
| Shearing (Peak) | N | 12.7 | 37.8 | 49.3 | 48.8 | 52.9 | 54.3 |
| Peeling (Peak) | N | 1.5 | 3.1 | 4.1 | 4.8 | 6.4 | 6.4 |
| Peeling (Energy) | N.mm | 5 | 12.3 | 16.7 | 23.8 | 21 | 22.7 |

METHOD FOR PROVIDING A LAMINATE WITH A HOOK AND LOOP FASTENING VOLUME, AND RESULTING LAMINATE

CROSS-REFERENCE TO RELATED CASES

This application is a continuation application of U.S. application Ser. No. 15/301,468, filed on Oct. 3, 2016, which is a 371 national phase application of PCT/EP2015/057441, filed on Apr. 7, 2015, which claims the benefit of French Priority Application Serial Numbers 1400848, filed on Apr. 8, 2014, and 1401591, filed on Jul. 16, 2014, all of which are incorporated herein by reference. Certified copies of the priority applications have been provided by the International Bureau in the case of U.S. application Ser. No. 15/301,468.

TECHNICAL DOMAIN

The present invention relates to a method for providing a laminate with a gripping capacity comprising at least one layer forming a support, for example a non-woven layer, and at least one non-woven layer with loops secured to the at least one lower layer forming a support. The present invention also relates to a device for providing a laminate of this type with a gripping capacity as well as to a laminate of this type.

A laminate comprising at least one layer forming a support, for example a non-woven layer, and at least one non-woven layer with loops, for example a carded non-woven fabric consolidated by calendering, is used in particular to form the looped part of a self-fastening hook and loop device, in particular for diapers and in particular to form a band disposed in the front part of the diaper in a central position on the belt, the band classically called the "landing zone", so as to enable the closure of the belt of the diaper by means of the engagement of hooks emanating from legs disposed in parts of lateral ends of the rear part of the diaper.

In the present invention, a gripping capacity is to be understood as meaning the available volume in the non-woven fabric with loops into which the hooks can penetrate in order to provide the engagement.

PRIOR ART

The gripping zones of the non-woven fabrics are produced in particular by assembling a strip of fibers over a non-woven support of the SMS type. The fibers are independent during production and a large quantity of fibers is needed to produce the gripping volumes and mainly only the fibers on the surface opposite the support can engage with the hooks. It is therefore necessary to have a large quantity of fibers and a significant weight of product in order to have satisfactory engagement with the hooks in order to meet the expectations of the user as regards performance. The large quantity of fibers also results in poor legibility of the printing produced on one of the faces of the SMS support.

There is, furthermore, a contradiction between the weight of the filaments used and the ability of the hooks to penetrate into the gripping zone. The greater the weight of fibers with the same volume that is used, the more difficult it is for the hooks to penetrate.

In general, a strip forming the landing zone is in the form of a laminate and comprises a support element, for example an SMS non-woven fabric, onto which can be printed, in particular, decorative patterns, and on the other hand a non-woven fabric with loops, for example a carded and calendered non-woven fabric that is secured to the upper part of the support element.

Preferably, the carded non-woven fabric must enable a user to see through the patterns printed onto the support element.

On the other hand, it is desirable for the engagement between the gripping loops formed by the textile element and the hooks to be optimal. In order to do this it is necessary for the hooks to be able to be introduced into or to engage easily in the gripping loops. Furthermore, good resistance to shearing of the loops when they are sought by a hook is preferable, as is good resistance to opening by peeling away. It is also desirable for the user to have a good fastening sensation upon opening that gives him or her confidence in the closure without any jolts and with a moderate effort. This appreciation is generally measured by calculating the peeling away energy. It is also desirable to obtain a good sensory quality associated with a sensation of softness that requires a soft touch and a textile appearance, as well as optimization of the weight of the landing zone, and so reduced cost of the product.

As a result there are requirements that contradict the desire for the printed patterns to be able to be seen well through the loop element which mean that the current landing zones, in particular those formed by two non-woven fabrics—respectively an SMS and a carded fabric—either do not exhibit good resistance to peeling away, whether this be the case in reality or is felt to be so by the user, or do not allow the user to see the printed patterns on the support layer well.

WO2008/130807 discloses a laminate comprising at least one supporting non-woven fabric and a carded non-woven fabric with loops that is secured to the support element. This laminate is produced by calendering, thus creating multiple connection zones. There is no gripping capacity.

OBJECT AND SUMMARY OF THE INVENTION

The object of the present invention is to overcome the disadvantages of the prior art by proposing a method for providing a laminate with a gripping capacity of the type defined above, intended in particular for forming a landing zone without thereby reducing the visibility of patterns printed on the support layer.

According to the invention, a method for providing a laminate with a gripping capacity, intended in particular for forming a landing zone, comprising at least one textile support element, in particular at least one non-woven fabric, for example SMS, and at least one non-woven fabric with loops, in particular a carded non-woven fabric, secured to the upper face of the support element, which comprises the steps wherein:

a strip of non-woven fabric with loops and a strip forming a support element are unrolled in order to pass them into a gap formed between an upper and a lower roller in order to secure the two elements to one another, the face of the upper roller in contact with the non-woven fabric with loops having, at the gap, a first speed orientated in the direction of unrolling the laminate, or in the direction of the machine or MD, the face of the lower roller in contact with the support element having, at the gap, a second speed likewise orientated in the direction of unrolling the laminate, or in the direction of the machine or MD, and characterized in that:

the first and the second speed are adjusted so that the first speed is greater than the second speed.

One thus obtains very simply a laminate which, while enabling excellent visibility of any patterns printed onto the support element, exhibits more hook and loop fastening volume and also a greater engagement ability for hooks.

According to a preferred embodiment of the invention, the first and the second speed are adjusted so that the ratio of the first speed to the second speed (or supercharging coefficient) is greater than 1.1, in particular greater than 1.2, and in particular between 1.2 and 1.6, preferably between 1.3 and 1.5.

Preferably, at least one of the two rollers is heated and the two strips are secured by calendering.

The present invention also relates to a laminate (1) comprising at least one support element (2), for example a non-woven fabric, in particular an SMS, and at least one non-woven fabric (3) with loops, in particular a carded non-woven fabric, secured to the support element (1), in particular by calendering with the first non-woven fabric, characterized in that the curve representing the force required to stretch the laminate along a given axis, for example the MD axis or the CD axis of the laminate, as a function of elongation, comprises a segment in which, starting from a zero elongation value, the force increases from zero up to a maximum force, corresponding in particular to the rupture of the laminate, and the curve comprises an inflection point (Pi) on said segment.

According to another embodiment, the support element is formed by a plastic film, in particular made of a thermoplastic material.

Preferably, the support element is not elastic. In a case where the support element is elastic, the curve representing the force as a function of deformation (elongation) that is appropriate to consider is the curve of the first deformation that starts from zero deformation.

BRIEF DESCRIPTION OF THE DRAWINGS

Purely as examples and as an illustration, embodiments of the invention will now be described, referring to the drawings in which.

PREFERRED EMBODIMENTS

Figure 1:
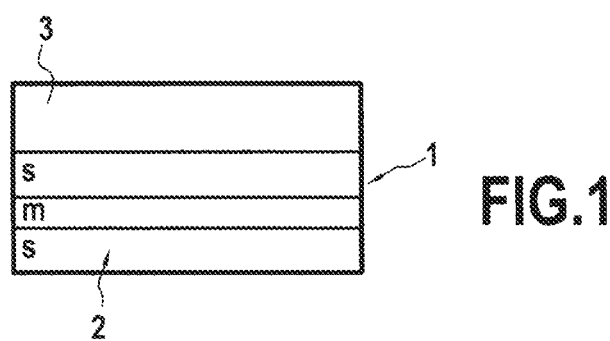
FIG. 1 shows a laminate according to an embodiment of the invention.

FIG. 1 shows a laminate 1 according to the invention, comprising a support element 2 formed by a layer of SMS non-woven fabric (i.e. made up of three superimposed non-woven layers—Spunbond-Meltblown-Spunbond) and an element 3 with loops formed by a carded non-woven fabric consolidated by calendering.

Figure 3:
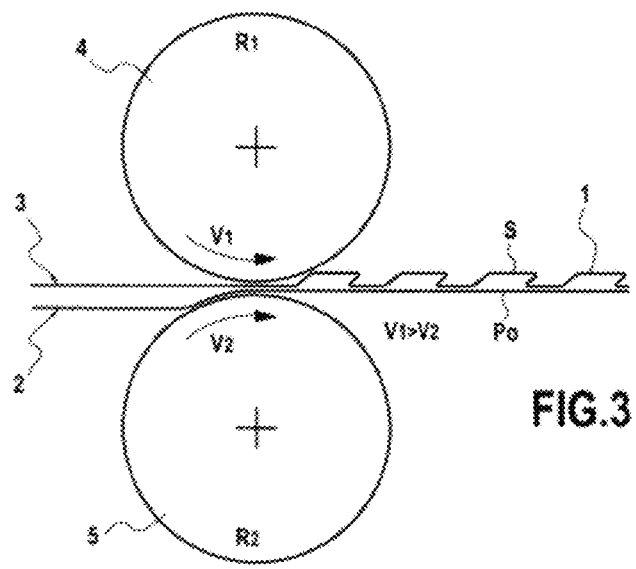
FIG. 3 is a basic diagram seen from the side of a device implementing the method according to the invention.

Patterns have been printed on the upper face of the support element 2, then the two elements 2 and 3 have been sent together through two rollers 4 and 5 in order to be mutually secured by calendering, as shown in FIG. 3. According to one version, one can print onto the lower face of the support element 2.

In the gap formed between the upper 4 and the lower 4 rollers, the two elements 2 and 3 are pressed one against the other by the respective external surfaces on either side of the two rollers. One or both of the rollers is/are heated and one of the two rollers comprises an engraving pattern.

The laminate 1 of FIG. 1 is that obtained at the output of the device shown in FIG. 3.

Furthermore, the respective speeds of the two lower and upper rollers at the point of contact with the laminate passing into the gap are orientated so as to be mutually parallel in the direction of unrolling the two elements, in particular in the machine direction or MD. However, the speed value V1 of the upper roller at the contact point with the textile element with loops in the gap is greater than that of the speed V2 of the lower roller, i.e. of the roller in contact with the support element. In order to obtain the laminate of FIG. 1, the V1/V2 ratio in FIG. 3 has been adjusted so that it is equal to 1.4.

As can be seen in FIG. 3, the element with loops comprises, in succession, connection zones, in particular formed by calendering, and zones forming the loops. The zones forming the loops are asymmetrical in form. In particular, their respective top or the middle S of their top part (in the case of a flattened top as in FIG. 3) is offset, in particular in the MD direction, with respect to the central point P0 equidistant from the two successive connection zones between which the respective zone forming loops extends. In other words, the right-hand segment SP0 is not perpendicular to the plane of the supporting non-woven fabric.

Figure 2:
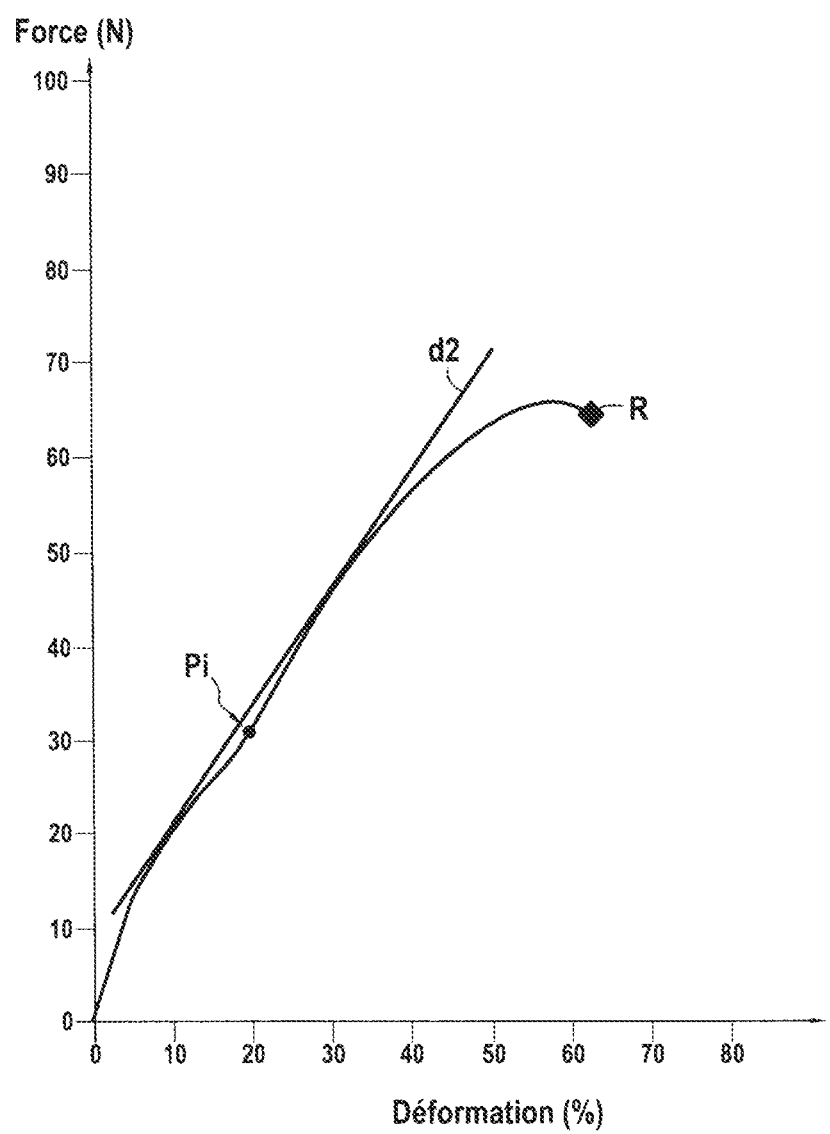
FIG. 2 shows a curve representing the stretching force as a function of the deformation of the laminate of FIG. 1.

FIG. 2 shows the curve representing the elongation force of the laminate 1 in the MD direction as a function of elongation. In order to produce this curve, the elongation at rupture test is used in the MD direction, which test consists of placing a sample with a length greater than 100 mm and a width of 50 mm of the laminate 1 obtained at the output of the device shown in FIG. 3 between two jaws (distance between the jaws equal to 100 mm) of a dynamometer (traction speed 50 mm/min).

As can be seen, the curve increases from 0% elongation to a point R at around 60% that corresponds to the maximum elongation force or else to the force at rupture. Beyond point R, the curve decreases, in particular with a steep gradient, very much greater in absolute value than the gradient of the segment between O and R.

In order to measure the inflection point one can use any classical method, for example graphically by the tangent method (d2) or by polynomial modelisation, in particular of row 4, of the curve.

On the segment between O and R, the curve comprises an inflection point Pi, at around 20%. The inflection point Pi is preferably greater than 4%, in particular between 7% and 30%, more preferably between 7 and 20%.

Figure 4:
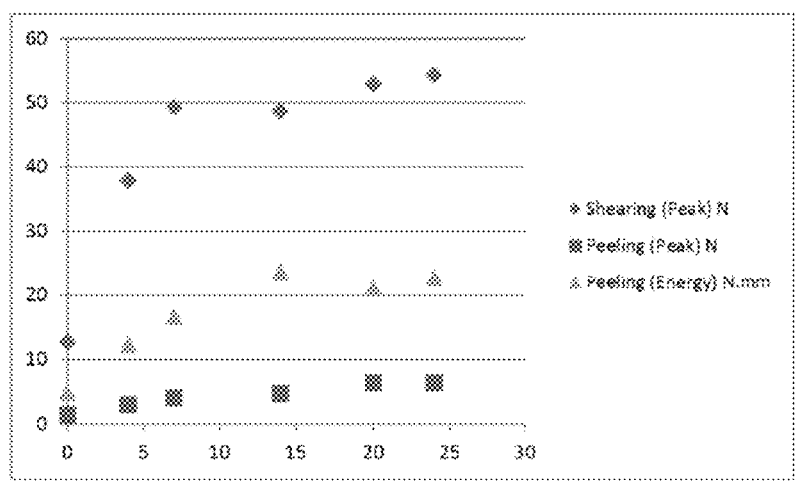
FIG. 4 shows the characteristic performance of a non-woven fabric as a function of the position in % of the inflection point.

As a function of the overfeeding, the gripping capacity will increase, thus enhancing the performance, in particular as regards shearing and peeling away, of the laminate, in particular of the landing zone, as shown by FIG. 4.

Figure 2A:
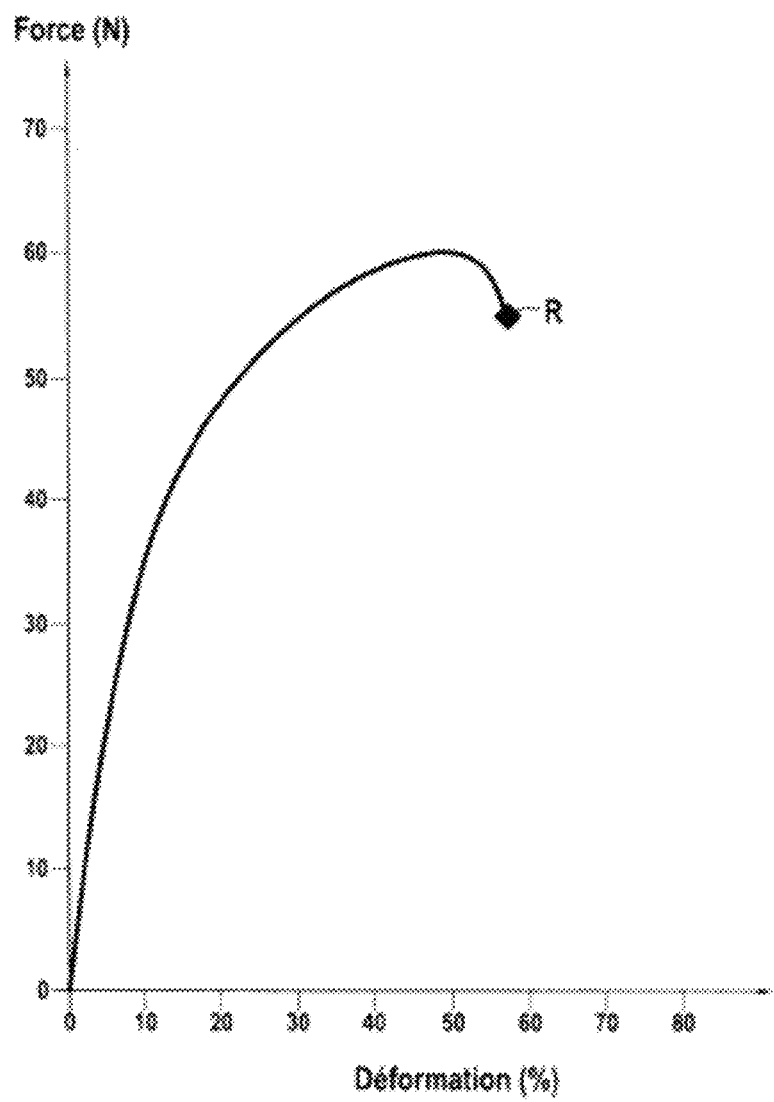
FIG. 2A shows the curve representing the force as a function of the deformation for a laminate of the prior art, in which no overspeed has been created during calendering.

As can be seen in FIG. 2A, if no overspeed is provided to any of the rollers (V1/V2=1), the curve does not comprise the inflection point. The resulting laminate does not have any gripping capacity.

Peeling Away Method

In order to measure the peeling away performance as a function of overfeeding, measurement of the resistance at the opening at 180° of an assembled hook/landing zone pairing is used. A strip of hooks that is 13 mm wide and 25.4 mm long assembled over an 80 $g/m^2$ paper support with a width of 25.4 mm is pressed onto a sample of the landing zone with dimensions of 50 mm×50 mm with the aid of a single 2 kg roller, the relative orientations of the products being identical to those used on the diaper. Traction of 1 kg is then applied for 10 seconds to the hook support so as to simulate the sealing of a diaper, in particular of a diaper that has elastic flaps. The paper supporting the hook is then inserted into the upper mobile jaw of a traction frame of the Synergie 200H type made by MTS System equipped with a 100 N dynamometric cell and the landing zone is inserted into the lower jaw. The distance between the two jaws is 50 mm. In order to measure the opening force, the upper part of the frame then executes translation from the bottom to the top at a speed of 305 mm/min. One then takes the value of the maximum force supplied by the machine as well as any energy value corresponding to the area below the surface of the test curve taken over the first 13 mm of the travel of the traction frame.

Shearing Method

In order to measure the shearing performance as a function of the overfeeding, a 50 mm×50 mm sample of landing zone is taken that is adhered over a rigid, for example, metallic plate with double-sided adhesive.

A strip of hooks that is 13 mm wide and 25.4 mm long and is assembled over a 250 g/m² paper support is engaged by the operator on the landing zone respecting the relative orientations of the products on the layer, and pressure is applied by the operator with his or her thumb for 3 secs.

1 kg traction is then applied for 5 seconds to the hook support so as to simulate the sealing of a diaper, in particular of a diaper that has elastic flaps.

The metallic plate supporting the landing zone is inserted into the mobile upper jaw of a traction frame of the DY 30 type made by MTS System equipped with a 100 N dynamometric cell.

The paper supporting the hook is then inserted into the fixed lower jaw.

The movement of the frame will be in the same direction as the 1 kg traction. The distance between the two jaws is 76 mm. In order to measure the opening force, the top part of the frame then executes translation from the bottom to the top at a constant speed of 305 mm/min. The test is carried out until the loop and the hook are totally disengaged. The maximum force value on the curve that is obtained is then taken.

In the present invention, non-woven fabric means a product obtained at the end of the formation of a strip of fibers and/or filaments which have been consolidated. The consolidation can be mechanical, chemical or thermal and is manifested by the presence of connections between the fibers and/or the filaments. This consolidation can be direct, i.e. made directly between the fibers and/or filaments by welding, or it can be indirect, i.e. by means of an intermediate layer between the fibers and/or the filaments, for example a layer of adhesive or a layer of binder. The term non-woven relates to a structure in the form of a lap or strip of fibers or filaments which are interlaced in a non-uniform, irregular or random manner. A non-woven fabric can have a single layer structure or a multiple layer structure. A non-woven fabric can also be joined to another material such as a film in order to form a laminate. A non-woven fabric can be made from different synthetic and/or natural materials. The natural materials are, for example, cellulose fibers such as cotton, jute, paper pulp, linen and the like, and can also include reprocessed cellulose fibers such as rayon or viscose. The natural fibers for a non-woven fabric can be prepared by using various processes such as carding. Synthetic materials include, but are not restricted to, for example, synthetic thermoplastic polymers which are known to form fibers that include, but are not restricted to, polyolefins, for example polyethyelene, polypropylene, polybutylene and the like; polyamide, for example polyamide 6, polyamide 6.6, polyamide 10, polyamide 12 and the like; polyesters, for example polyethylene teraphthalates, polybutylene terephthalates, polylactic acids and the like, polycarbonates, polystyrenes, thermoplastic elastomers, polymer vinyls, polyurethanes and mixtures and copolymers of the latter.

In general, the fibers and the filaments differ mainly by their length and by their production method.

Filaments mean the unitary elements, with very great lengths with respect to the diameter to which their section is assigned, extruded continuously in order to directly form a strip of non-woven fabric that can then be consolidated by thermo-linking or any other means so as to make it possible to achieve the desired performance and/or their transportation. Preferably the filaments exhibit a length greater than 120 mm.

Fiber is understood to be the generic term designating a textile material or a textile material element with reduced length less than the length of the filaments and able to be spun and/or used in the production of non-woven fabrics. A distinction can be made between two types of fiber—short fibers formed discontinuously with a small length of less than 70 mm (preferably 25 mm to 60 mm) and long fibers formed discontinuously with a large length of greater than 70 mm (preferably 80 mm to 120 mm).

Unlike filaments that are consolidated directly after having been extruded, fibers are collectively aligned and organized in a strip during a carding step that is well known to the person skilled in the art. This strip can then be consolidated by thermal linking or by any other means so as to make it possible to achieve the desired performance and/or their transportation. According to the invention one can advantageously use a non-woven fabric with loops that comprises high elongation fibers.

High elongation fibers are understood to mean fibers which exhibit maximum elongation before rupture of more than 250%, i.e. fibers which can stretch by at least 2.5 times their length at rest and before stretching.

More specifically, high elongation fibers exhibit maximum elongation before rupture of more than 300% elongation, or else exhibit maximum elongation before rupture of between 300% and 600% elongation, more specifically between 450% and 500% elongation.

According to one embodiment, the non-woven fabric with loops comprises high elongation fibers, in particular at least 50% high elongation fibers.

According to the present invention loop means a filament and/or a fiber that comprises two ends, each one joined to the support at a respective point of the support or at a same point of the support. A loop can also be formed from a number of filaments or fibers that are joined to one another and of which at least two are joined to the support at one point or at two respective distinct points. The loops can exhibit a specific dissymmetrical form here.

Non-woven fabric with loops means a non-woven fabric forming loops that is available to a hook after being joined to the support.

In one version, one could envisage activating the non-woven fabric with loops before securing it to the support element.

Preferably, at least one support element is a non-woven fabric, in particular an SM (Spunbound-Meltblown), an SMS (Spunbond-Meltblown-Spunbond), or an SMMS (Spunbond-Meltblown-Meltblown-Spunbond), SSMMS (Spunbond-Spunbond-Meltblown-Meltblown-Spunbond) and the like.

According to the invention, elastic is understood as meaning an element that, according to the test described below, has a persistence or SET' of less than 15%, preferably less than 10%, more preferably less than 5% for a stretch of 100% of its initial dimension. According to the invention, non-elastic is understood as meaning an element that does not come under the above definition of an elastic element. Likewise, an element that breaks before reaching elongation of 100% of its initial dimension must be considered to be non-elastic.

One can also, for example, measure the elasticity of a laminate by determining its persistence by the following test:

The sample is conditioned in a normal atmosphere as defined in standard ASTDM 5170 at a temperature of 23° C.±2° C. and relative humidity of 50%±5%.

As equipment, a dynamometer according to standard EN 10002, in particular the Synergie 200, a column available from the company MTS Systems Corp, U.S.A., along with TESTWORKS 4.12. operating software is used.

The sample is prepared by cutting the elastic product (for example the laminate of the invention) with a cutter or scissors into a sample that is 50 mm wide in the MD direction (direction of the machine perpendicular to the plane of FIG. 1) and 120 mm long in the CD direction (the transverse direction, or horizontal direction in FIG. 1).

The parameters are selected as follows:
Distance between jaws: 100 mm
Machine speed: 508 mm/mn
Number of cycles: 1
Elongation of the product: 100% at constant speed The product is stretched 100% by vertical displacement of the upper jaw, the lower jaw being fixed, then it is kept in this position for 30 seconds, then it is returned to the initial position at constant speed where it is left for 60 seconds (end of the cycle), then it is stretched again until the product ruptures.

One then obtains the curve representing the stretching force as a function of elongation in %, and this exhibits a hysteresis that allows one to determine the "Set" by means of the following calculation formula:

$$SET = L1 - L0$$

With:
L0: Intersection point with the axis of the Xs (elongation in %) upon starting the test, i.e. at the start of the cycle.
L1: Intersection point with the axis of the Xs (elongation in %) upon starting the second elongation after the return to a zero force and waiting for 60 seconds.

Key to the Wording on the Figures:
FIGS. 2 and 2A
  Déformation=deformation
FIG. 3
  Sur-alimentation machine=overfeeding machine
  Consigne=set point
  Point inflexion=inflection point
  Cisaillement (Pic)=shearing (peak)
  Pelage (Pic)=peeling away (peak)
  Pelage (Energie)=peeling away (energy)
FIG. 4
  Cisaillement (Pic)=shearing (peak)
  Pelage (Pic)=peeling away (peak)
  Pelage (Energie)=peeling away (energy)

The invention claimed is:

1. A laminate comprising at least one support element in the form of a non-woven fabric comprising at least a Spunbond layer having a lower face and an upper face, and at least one non-woven fabric with loops made of a material comprising synthetic thermoplastic polymers, having a lower face and an upper face, wherein said upper face of the at least one support element in the form of a non-woven fabric is secured to said lower face of the non-woven fabric with loops, said at least one non-woven fabric with loops is a product obtained at the end of the formation of a strip of fibers and/or filaments which have been consolidated, said non-woven fabrics with loops comprising fibers and/or filaments and connections between the fibers and/or the filaments made directly by welding or indirectly by means of a layer of adhesive or a layer of binder, wherein the curve representing the force required to stretch the laminate along a given axis of the laminate, as a function of elongation, comprises a segment in which, starting from a zero elongation value, the force increases from zero up to a maximum force, wherein said maximum force corresponds to the rupture of the laminate, and the curve comprises an inflection point (Pi) on said segment, wherein a top of a zone forming loops or a middle(S) of a top part, wherein the top part is a flattened top, is offset in a machine direction, with respect to a central point (P0) equidistant from the two successive connection zones between which the zone forming loops extends.

2. The laminate of claim 1, wherein, when measuring the resistance at the opening at 180° of an assembled pairing made of hooks and of the laminate, wherein a strip of hooks, being 13 mm wide and 25.4 mm long assembled over an 80 g/m² paper support with a width of 25.4 mm, is pressed onto the loops side of the laminate with dimensions of 50 mm×50 mm with the aid of a single 2 kg roller, traction of 1 kg being then applied for 10 seconds to the hooks support so as to simulate the sealing of a diaper, the paper supporting the hooks being then inserted into an upper mobile jaw of a traction frame of a dynamometer equipped with a 100 N dynamometric cell and the laminate being inserted into a lower fixed jaw, a distance between the two jaws being 50 mm, in order to measure an opening force, the upper part of the frame then executing a translation from the bottom to the top at a speed of 305 mm/min, and the value of the maximum force supplied by the machine being comprised between 3.1N and 6.4N.

3. The laminate of claim 1, wherein, when a 50 mm×50 mm sample of the laminate is taken to be adhered to a metallic plate with double-sided adhesive, a strip of hooks, being 13 mm wide and 25.4 mm long assembled over a 250 g/m² paper support, being engaged on the loops side of the laminate, and a 1 kg traction being then applied for 5 seconds to the hooks support so as to simulate the sealing of a diaper, the metallic plate supporting the laminate being inserted into a mobile upper jaw of a traction frame of a dynamometer equipped with a 100 N dynamometric cell and the paper supporting the hooks being then inserted into a lower fixed jaw, the movement of the frame being in the same direction as the 1 kg traction, a distance between the two jaws being 76 mm, in order to measure an opening force, the top part of the frame then executing a translation from the bottom to the top at a constant speed of 305 mm/min, the test being carried out until the loops and the hooks are totally disengaged, a maximum force value being comprised between 37.8N and 54.3N.

4. The laminate of claim 2, wherein, when a 50 mm×50 mm sample of the laminate is taken to be adhered to a metallic plate with double-sided adhesive, a strip of hooks, being 13 mm wide and 25.4 mm long assembled over a 250 g/m² paper support, being engaged on the loops side of the laminate, and a 1 kg traction being then applied for 5 seconds to the hooks support so as to simulate the sealing of a diaper, the metallic plate supporting the laminate being inserted into a mobile upper jaw of a traction frame of a dynamometer equipped with a 100 N dynamometric cell and the paper supporting the hooks being then inserted into a lower fixed jaw, the movement of the frame being in the same direction as the 1 kg traction, a distance between the two jaws being 76 mm, in order to measure an opening force, the top part of the frame then executing a translation from the bottom to the top at a constant speed of 305 mm/min, the test being carried out until the loops and the hooks are totally disengaged, a maximum force value being comprised between 37.8N and 54.3N.

5. The laminate of claim 1, wherein the at least one support element in the form of a non-woven fabric is not elastic.

6. The laminate of claim 1, wherein the inflection point (Pi) is greater than 4%.

7. The laminate of claim 2, wherein the inflection point (Pi) is greater than 4%.

8. The laminate of claim 1, wherein the support element in the form of a non-woven fabric and the non-woven fabric with loops are secured by calendering.

9. The laminate of claim 1, wherein the non-woven fabric with loops is a carded non-woven fabric.

10. The laminate of claim 1, wherein that the non-woven fabric with loops comprises fibers with high elongation.

11. A laminate comprising at least one support element in the form of a non-woven fabric comprising at least a Spunbond layer having a lower face and an upper face, and at least one non-woven fabric with loops made of a material comprising synthetic thermoplastic polymers, having a lower face and an upper face, wherein said upper face of the at least one support element in the form of a non-woven fabric is secured to said lower face of the non-woven fabric with loops, wherein the non-woven fabric with loops comprises, in succession, connection zones and zones forming the loops, wherein within the zones forming the loops, the loops are asymmetrical in form, and said at least one non-woven fabric with loops is a product obtained at the end of the formation of a strip of fibers and/or filaments which have been consolidated, said non-woven fabrics with loops comprising fibers and/or filaments and connections between the fibers and/or the filaments made directly by welding or indirectly by means of a layer of adhesive or a layer of binder, wherein the curve representing the force required to stretch the laminate along a given axis of the laminate, as a function of elongation, comprises a segment in which, starting from a zero elongation value, the force increases from zero up to a maximum force, wherein said maximum force corresponds to the rupture of the laminate, and the curve comprises an inflection point (Pi) on said segment.

12. The laminate of claim 11, wherein the at least one support element in the form of a non-woven fabric is not elastic.

13. The laminate of claim 11, wherein the support element in the form of a non-woven fabric and the non-woven fabric with loops are secured by calendering.

14. The laminate of claim 11, wherein the non-woven fabric with loops is a carded non-woven fabric.

15. The laminate of claim 11, wherein that the non-woven fabric with loops comprises fibers with high elongation.

16. A method for providing gripping capacity to a laminate comprising at least one support element in the form of a non-woven fabric comprising at least one Spunbond layer, having a lower face and an upper face, and at least one non-woven fabric with loops, having a lower face and an upper face, wherein the lower face of the at least one non-woven fabric with loops is secured to the upper face of the at least one support element in the form of a non-woven fabric, and said at least one non-woven fabric with loops is a product obtained at the end of the formation of a strip of fibers and/or filaments which have been consolidated, said non-woven fabrics with loops comprising fibers and/or filaments and connections between the fibers and/or the filaments made directly by welding or indirectly by means of a layer of adhesive or a layer of binder; the method comprising the steps of:

unrolling a strip of the non-woven fabric with loops and a strip of the support element in the form of a non-woven fabric in order to pass them into a gap formed between two upper and lower rollers in order to secure the support element in the form of a non-woven fabric and the non-woven fabric with loops to one another, wherein at the gap, a face of the upper roller coming in contact with the upper face of the non-woven fabric with loops has a first speed orientated in a direction of unrolling of the laminate, or in a machine direction or MD, and wherein at the gap, a face of the lower roller coming in contact with the lower face of the support element in the form of a non-woven fabric has a second speed orientated in the same direction of unrolling of the laminate, and wherein the first and second speeds are adjusted so that the first speed is greater than the second speed, wherein the first and the second speeds are adjusted so that the ratio of the first speed to the second speed (or the overfeeding coefficient) is between 1.1 and 1.6, so that a top of a zone forming loops or a middle(S) of a top part, wherein the top part is a flattened top, is offset in a machine direction, with respect to a central point (P0) equidistant from the two successive connection zones between which the zone forming loops extends.

17. The method of claim 16, wherein the overfeeding coefficient is between 1.2 and 1.5.

18. The method of claim 16, wherein at least one of the two rollers is heated and the two strips are secured by calendering.

* * * * *